United States Patent [19]

Kruse et al.

[11] 4,435,586

[45] Mar. 6, 1984

[54] ETHERIFICATION PROCESS FOR HEXITOLS AND ANHYDROHEXITOLS

[76] Inventors: Walter M. Kruse, 1 Woodbury Ct., Wilmington, Del. 19805; John F. Stephen, 200 William Penn Blvd., West Chester, Pa. 19380

[21] Appl. No.: 372,623

[22] Filed: Apr. 28, 1982

[51] Int. Cl.$^3$ .................. C07D 493/04; C07D 307/20
[52] U.S. Cl. .................................... 549/464; 549/476; 568/672
[58] Field of Search ................. 549/464, 476; 568/672

[56] References Cited

U.S. PATENT DOCUMENTS 2,234,200  3/1941  Soltzberg ........................... 568/672
2,420,519  5/1947  Brown ................................. 549/464
3,840,605  10/1974 Gordon ........................... 260/614 R
4,322,359  3/1982  Hillard et al. ....................... 549/464
4,374,282  2/1982  Maldonado et al. ................ 568/672

FOREIGN PATENT DOCUMENTS 510423   10/1930  Fed. Rep. of Germany.
258870   12/1967  Fed. Rep. of Germany.
3038996  4/1981   Fed. Rep. of Germany.
988123   8/1963   United Kingdom.

OTHER PUBLICATIONS

Haworth, J., Chem. Soc., vol. 107 (1915), pp. 8-16.
Benedict et al., Synthesis, Jun. 1979, pp. 428-429.
Muskat, J. Am. Chem. Soc., vol. 56 (1934), pp. 693-695.
Smith et al., Canadian J. of Chem., vol. 47 (1969), pp. 2015-2019.
Freedman et al., Tet. Letters No. 38, (1975), pp. 3251-3254.

Primary Examiner—Henry R. Jiles
Assistant Examiner—Bernard Dentz
Attorney, Agent, or Firm—Richard A. Rowe

[57] ABSTRACT

A high yield process for the polyalkylation of hexitols and hexitol inner ethers is presented wherein aqueous dispersions of monoalkali metal alkoxides thereof in organic solvent are reacted with alkyl monohalides to first form the monoalkylated hexitols or hexitol inner ether and thereafter further alkylated by addition of reactants to form the completely alkylated derivative.

9 Claims, No Drawings

ETHERIFICATION PROCESS FOR HEXITOLS AND ANHYDROHEXITOLS

This invention is related to an improved high yield/low pressure process for polyetherification of hexitol $C_6H_8(OH)_6$; hexitan $C_6H_8O(OH)_4$ and hexide $C_6H_8O_2(OH)_2$ by the reaction of monoalkali metal alkoxides of these compounds with low molecular weight alkyl halides in aqueous solutions dispersed in organic solvents. It includes conducting the reaction in a mixture with organic solvents and phase transfer catalysts.

In general the method of the invention can be considered an improved process for conducting the interaction of alkaline metal alkoxide with an alkyl halide which is traditionally referred to as the Williamson ether synthesis. Completely etherified anhydrohexitol derivatives have been described in U.S. Pat. Nos. 2,234,200 and 2,420,519. The earlier patent describes a technique for carrying out the synthesis in liquid ammonia while the latter case is directed to the treatment of alkali solutions of sorbide (isosorbide) (dianhydro-sorbitol) with dimethyl sulfate. In traditional commercial procedures the polyhydroxy derivatives have been treated with excess sodium hydroxide and thereafter reacted with alkyl chloride at temperatures of 120° C. and at pressures above 100 pounds per square inch. Such high temperature reactions require special equipment, involve a sizeable amount of decomposition, form products which are off color and offer poor yields because of incomplete alkylation and the difficulty of separating pure products from the reaction mixture.

The present invention is directed to the stepwise alkylation of hexitol and anhydrohexitol derivatives in aqueous media dispersed in organic solvent. The description of an anhydrous procedure for conducting the Williamson ether synthesis in dimethylsulfoxide has been described by Smith, Vanderpool and Culak, *Canadian J. Chem.*, 47, 1969, pages 2015–2019. When their anhydrous technique is carried out in the presence of a slight excess of solid sodium hydroxide, a large amount of dimethylsulfoxide and applied to hexitols and hexitol anhydrides, the reaction is very slow and does not go to completion. An anhydrous synthesis of aliphatic ethers in dimethylsulfoxide employing potassium hydroxide and alkyl bromide or sulfate is described by Benedict, Bianchi, and Cate in *Synthesis*, June 1979, page 428 and 429. Alkylation of primary alcohols has been demonstrated using potassium hydroxide powder and alkyl bromides and iodides in anhydrous dimethylsulfoxide at room temperature by Johnstone and Rose in *Tetrahedron*, 35, (1979), pages 2169–2172. Reactions conducted with bromides and iodides are too expensive for commercial synthesis.

A recently issued patent U.S. Pat. No. 4,322,359 is directed to adding an excess of dimethyl sulfate to inner ethers of sorbitol in organic solvent at low temperature. Another process for alkylating primary alcohols in organic solvent using a phase transfer catalyst employing excess aqueous alkali, alkyl chloride in organic solvent is described by Freedman and Dubois, *Tetrahedron Letters* No. 38, pp. 3251–3254 (1975).

It is an object therefore of the present invention to provide for a high yield process for the polyalkylation of hexitols and inner ethers of hexitols such as hexitans and hexides or isohexides to form polyalkyl ethers by displacing the hydrogen on the hydroxyl groups of these materials with alkyl groups having from 1–4 carbon atoms by (a) forming an aqueous solution of the hexitol dispersed in organic solvent (b) forming a monoalkali metal alkoxide by the addition of substantially stoicheometric amounts of sodium or potassium alkali, (c) forming a monoalkyl ether by the addition of an alkylmonohalide having 1–4 carbon atoms to the solution, (d) completing the polyalkylation by adding more alkylmonohalide with the addition of substantially stoicheometric amounts of hydroxide such that no more than a monoalkali metal alkoxide derivative is present in the solution, and (e) separating the polyalkyl ether from the reaction mixture. It is a further object to provide for a process wherein steps (a) thru (d) is carried out in the presence of a reaction promoter such as a phase transfer catalyst. Another object includes a process for performing steps (a) thru (c) sequentially.

The process of the invention is particularly useful in preparing fully methylated, ethylated, propylated and butylated polyethers of hexitols such as sorbitol and mannitol. In particular it is useful in preparing hexamethyl hexitols and dimethylisosorbide. The anhydrohexitols are inner ethers resulting from splitting off one or two moles of water from hexitol, a six carbon straight chain hexahydric alcohol. The removal of one molecule of water results in the formation of a hexitan such as sorbitan or mannitan which are useful starting materials in the preparations of the tetralkyl ether of sorbitan and mannitan such as tetramethyl and tetraethyl sorbitan. The tetramethyl sorbitan has specific solvent properties and can be used as a solvent in the preparation of certain pharmaceutical bases. The removal of two molecules of water from a hexitol results in the formation of a hexide or isohexide which are diinnerethers such as sorbide or isosorbide, mannide or isomannide. In particular the process can be applied to the manufacture of dimethyl, diethyl, dipropyl, diisopropyl, diisobutyl, dibutyl isosorbide. Such derivatives are particularly useful as solvents with special attention drawn to dimethyl isosorbide which has application in the preparation of pharmaceutical ointment and gels.

Less common hexitol isomers such as dulcitol, iditol, talitol and their inner ethers can be used as starting materials in proportions similar to those described for sorbitol and mannitol and their corresponding anhydro and dianhydro inner ethers to provide polyalkylated derivatives.

As alkylating agent may be employed a monoalkyl chloride selected from methyl, ethyl, propyl, isopropyl, butyl, and isobutyl chloride. The equivalent bromide and iodide may also be used if economical. The term alkyl halide refers to these compounds.

Polar aprotic solvents such as dimethyl formamide, dimethylacetamide, and dimethylsulfoxide may be used as dispersing agent for carrying out the reaction provided that the water concentration does not exceed about 50%.

For example, dimethyl sulfoxide $(CH_3)_2SO$ (DMSO) is available commercially and may be used as the solvent when aqueous alkali is added thereto or as an aqueous mixture when the mol ratio of water to dimethyl sulfoxide does not exceed 10/1.

Sodium hydroxide or potassium hydroxide may be added as alkali in aqueous solution, dry powder or granules. In place of the hydroxide may be used the equivalent carbonates with somewhat lower activity. In the practice of this invention it is preferred to use a concentrated aqueous solution of potassium or sodium hydroxide and most preferred is a 50% aqueous solution thereof.

In general the invention is carried by first forming a an aqueous solution of the hexitol or hexitol inner ether dispersed in an organic solvent such as dimethyl formamide, dimethyl acetamide, dimethylsulfoxide, toluene, xylene, ethylene glycol diethylether, bis(2-methoxyethyl)ether and the like. This solution is heated to a temperature of at least about 60° C. and most preferably 80°–90° C. and thereafter agitated employing efficient mixing during the addition of the alkali such that a homogeneous mixture is maintained. The addition of alkali is controlled such that the temperature of the reaction mix does not exceed 100° C. Alkyl halide may be added after or simultaneously with the addition of alkali.

The rate of addition of alkali to the reaction mixture is carried out such that no more than a monoalkali metal alkoxide of the hexitol or hexitol ether is formed in the reaction mixture. This is a critical feature of the invention in that the formation of the dialkali metal alkoxide may result in the formation of an insoluble derivative which separates from the reaction mix.

Upon completion of the reaction to form the fully alkylated hexitol or hexitol inner ether derivative the reaction mix is cooled and extracted with aromatic hydrocarbons, ethers, esters, ketones or nitriles and in the case of dimethyl isosorbide most preferably toluene or ethyl benzene to remove the alkylated product from the aqueous alkali metal salt solution. The pure derivative is then separated from the solvent extract by distillation.

It has been found that the reaction is more effectively carried out in a dispersion of an aromatic solvent such as toluene or aprotic solvent such as diemthylsulfoxide. An unexpected advantage offered by carrying out the reaction with isosorbide to form dimethyl isosorbide in DMSO is that two phases are formed after cooling and the addition of toluene produces an immiscible toluene/dimethyl isosorbide layer and dimethyl sulfoxide/water/alkali chloride salt layer.

The reaction may be carried out in relatively small amounts of solvent. For example, when dimethylsulfoxide is used in the preparation of dimethyl isosorbide excellent results are obtained when the molar ratio of dimethylsulfoxide to isosorbide in the starting mixture ranges from 0.2–1. A most preferred ratio is 0.4–0.8.

When the reaction is run in a dispersion of an aromatic solvent such as toluene it is advantageous to employ a phase transfer catalyst. The use of phase transfer catalyst in promoting the Williamson synthesis is known for hydrophilic alcohols at a temperature below 60° C. Such catalytic materials include quarternary ammonium and phosphonium salts, tertiary amines which are transformed into quarternary ammonium salts during the reaction, strongly basic quarternary ammonium polystyrene type ion exchange resins, and polyethylene glycols or their mono and dialkyl ethers. When the reaction is carried out at temperatures below 85°, quarternary ammonium salts such as tetrabutyl ammonium sulfate, tributylhexadecyl phosphonium bromide, tetraethyl ammonium bromide, methyltrioctyl ammonium chloride, cetyltrimethyl ammonium bromide, benzyltrimethyl ammonium chloride, cetylpyridinium chloride can be useful. A certain ion exchange media such as Amberlite IRA-400 C.P. a strongly basic, quarternary ammonium (polystyrene) type (aminated with trimethylamine) anion exchange resin of medium porosity is also effective as catalyst. Poly(ethylene glycols) and their dimethyl ethers are also useful catalysts. These catalysts are employed based on the weight of the hexitol or hexitol inner ether in concentrations ranging from 1–10 mol %.

The solvent which contains the alkylated hexitol derivative may be then distilled under low pressure conditions to recover the pure derivative. It is for this reason that solvents having a boiling point in the range of 100°–190° C. be employed such that they may be separated from the product by vacuum distillation. Suitable solvents such as ethylene glycol diethyl ether (b.p. 121° C.), bis(2-methoxyethyl) ether (b.p. 160°–163° C.) and toluene (b.p. 110° C.).

The following examples are carried out in a four-neck, 2-liter flask provided with a gas sparger a three inch Teflon stirrer (driven by an electric motor regulated by a Variac), a thermocouple connected to a temperature controller which regulates the heat input into the heating mantle, a dropping funnel and a condenser (equipped with a water separator for Example 2) which is connected via a mercury bubbler to a dry ice trap for condensing unreacted methyl chloride when it is used as a methylating agent. Careful control of methyl chloride flow allows only a small amount of methyl chloride to escape the reactor. Controlling the gas flow is also achieved by placing the methyl chloride cylinder in a controllable cold bath. The boiling point of methyl chloride is −24° C. and has a vapor pressure at 0° of 22 psi (1,919 millimeters Hg). Of course in commercial equipment the reaction may be carried out at pressures higher than atmospheric pressure and corresponding higher temperatures of 120° C. or thereabouts.

EXAMPLE 1

Hexamethyl sorbitol 182 g sorbitol (1 mole) and 300 milliliters dimethyl sulfoxide (DMSO) were charged to the flask described above. The Variac was set such that the stirrer turned at about 650 rpm. The mixture was heated to a temperature of 80° C. at which time methyl chloride was slowly added and 50% aqueous sodium hydroxide solution was permitted to drop into the solution. The temperature was permitted to rise to 85° C. and held at that temperature as near as possible throughout. The addition of 160 g 50% sodium hydroxide solution (2 moles) was completed after one hour. 160 g (4 moles) sodium hydroxide pellets in portions of about 20 g were added over a period of two hours. The reaction mixture was then cooled to room temperature and filtered to remove sodium chloride precipitate. The filtrate was returned to the reactor and heated again to 85° C. after which two 20 g portions of sodium hydroxide pellets were added and stirred for an additional four hours under continuous methyl chloride sparging. Analysis indicated the formation of penta and tetramethyl sorbitol. The reaction mixture again was filtered and the filtrate was concentrated to remove water. The concentrated filtrate was placed back into the reactor with an additional 100 ml DMSO added and after the temperature had reached 85° C. 80 grams of 50% sodium hydroxide was added and methyl chloride sparging continued. After 1.5 hours the reaction was complete with the formation of hexamethyl sorbitol. The salt was removed by filtration and the filtrate was three times extracted with 300 ml portions of toluene in a two liter separatory funnel. After intensive shaking two phases separated within a few minutes after which the toluene layer was removed and collected.

The toluene was removed by distillation in a rotary evaporater whereupon hexamethyl sorbitol containing less than about 0.5% DMSO and toluene remained. The hexamethyl sorbitol is distilled at 121° C. under 5 mm Hg pressure. 175 g of hexamethyl sorbitol (67% yield) having a refractive index 1.43564 (20° C.) and a viscosity of 10.3654 centipoises (20° C.).

EXAMPLE 2

Tetramethyl 1,4 Sorbitan 364 g sorbitol (2 moles), 600 ml toluene and 1 g concentrated sulfuric acid were placed into the equipment described above. The reaction mixture was heated to reflux temperature and 40 ml water (2.2 moles) was collected by azeotropic distillation within 6 hours. The toluene phase was decanted and the sorbitan formed was dissolved in 300 ml DMSO and placed into the reactor together with 3 ml 50% sodium hydroxide.

The reaction mixture was brought to 85° C. Methyl chloride was added through the sparger system and 480 g of 50% sodium hydroxide (6 mole) solution was added over a period of two hours. An additional 80 g of hydroxide pellets were added in 10 g portions over the next two hours. The mixture was cooled and filtered to remove sodium chloride after which the filtrate was added to the flask and heated to 85° C. with an additional 80 g of sodium hydroxide (2 moles) pellets added at 85° C. over a period of one hour.

The reaction mixture was cooled extracted with toluene and distilled as described in Example 1 to yield a 185 g portion (43%) tetramethyl 1,4 sorbitan by distillation at 120° C. at 6 mm Hg. Refractive index 1.44543 (20° C.); viscosity 7.4768 centipoise (20° C.).

EXAMPLE 3

Dimethyl Isosorbide 300 g isosorbide (2 moles) and 165 g DMSO charged into the equipment described above and heated to 80° C. Methylchloride gas was passed into the reaction mixture through the sparger and 480 g of 50% sodium hydroxide solution (6 moles) was added dropwise. The temperature went to 85° C. and was controlled at that temperature by control of the sodium hydroxide addition. The agitator was operated at 650 rpm to achieve good liquid gas mixing. The addition of sodium hydroxide solution was complete within two hours. The reaction was terminated after an additional two hours, cooled and filtered to remove sodium chloride precipitate. The filtercake was washed with 300 ml of toluene which was added to the filtrate which was placed in a 2 liter separatory funnel. After a brief intensive shaking two phases separated within minutes. The aqueous layer was again extracted with 300 ml toluene for the second extraction and again with 200 ml toluene for the third extraction. To avoid the filtration of sodium chloride 300 ml of toluene can be added to the vigorously stirred reaction mixture. After the stirring was stopped the toluene phase was syphoned off to remove the produced dimethyl isosorbide from the aqueous DMSO/sodium chloride salt phase. The phase separation can be speeded up by addition of a minor amount of acid to the aqueous phase. After removal of toluene in the rotary evaporator 180 g dimethyl isosorbide was distilled at 21 mm Hg pressure at 125° C. for a yield of about 83.5%.

EXAMPLE 4

Dimethyl Isosorbide

In equipment described above was placed 400 ml toluene 20.4 g (60 millimoles, 3 mole percent) tetrabutyl ammonium hydrogen sulfate, 300 grams isosorbide (2 moles) which was heated under stirring (at least 650 rpm) to 85° C. Methyl chloride gas was added and the addition of 480 g sodium hydroxide (50% solution) was added over a period of two hours. The reaction dispersion was permitted to agitate for an additional five hours after which it was cooled and filtered to remove sodium chloride. The filtrate was placed in a 2 liter separatory funnel and the layers permitted to separate. The aqueous phase was separated and extracted with 2 portions of 200 ml of toluene. The organic phase and toluene washes were combined and washed with 200 ml of 50% sulfuric acid. The toluene phase after separation was placed in a rotary evaporator after which the residue was distilled to remove dimethyl isosorbide in a yield of about 80.5%.

Examples 3 and 4 were repeated for Examples 5-18 using varying amounts of ingredients and are listed in Tables 1 and 2. Total yields as reported in Column 6 were determined by gas-liquid chromatographic (GLC) techniques from samples of the reaction mix. Recovered yields are reported in the Table. Examples 19-24 listed in Table 3 describe a one pot technique starting with sorbitol to produce isosorbide which is then methylated and recovered from the pot by direct distillation therefrom.

TABLE 1

| | DMI Process using Phase Transfer Catalyst | | | | | |
|---|---|---|---|---|---|---|
| Example No. | Reagents | Isosorbide: base, mole ratio | React Time hrs. | Temp. °C. | DMI % Total Yield GLC est. | Isolated Distilled Yields |
| 5 | 2 mole isosorbide + 7 mole NaOH + 400 ml toluene + 20.4 g (60 mmole) TBAHSO$_4$ | 1:3.5 | 7.5 | 86 | 90% | 280 g (80.5%) |
| 6 | 2 mole isosorbide + 7 mole NaOH + 300 ml ethylene glycol diethyl ether solvent + 20.4 g TBAHSO$_4$ | 1:3.5 | 7.5 | 85 | 80% | 269.4 g (77.2%) |
| 7 | 2 mole isosorbide + 7 mole NaOH + 400 ml toluene + reused catalyst (TBAHSO$_4$) | 1:3.25 | 7.5 | 85 | 80% | 261 g (75%) |
| 8 | 2 mole isosorbide + 7 mole NaOH + 400 ml toluene + 9.6 g TBABr (Tributylamine Bromide) | 1:3.5 | 7.0 | 85 | 80% | 268.4 g (77%) |
| 9 | 2 mole isosorbide + 7 mole NaOH + 400 ml toluene + 20 g (TBAHSO$_4$) | 1:3.5 | 7.5 | 85 | 80% | 261.7 g (75%) |
| 10 | 2 mole isosorbide + 300 ml toluene + 60 g poly(ethylene glycol) ether MW 600 | 1:3.5 | 10.0 | 85 | 80% | 261.2 g (75%) |

TABLE 1-continued
DMI Process using Phase Transfer Catalyst

| Example No. | Reagents | Isosorbide: base, mole ratio | React Time hrs. | Temp. °C. | DMI % Total Yield GLC est. | Isolated Distilled Yields |
|---|---|---|---|---|---|---|
| 11 | catalyst + 7 mole KOH 2 mole isosorbide + 7 mole NaOH + 400 ml toluene 20 g tributylamine | 1:3.5 | 7.5 | 85 | 80% | 261.7 g (75%) |

TABLE 2
DMI Process using DMSO as Solvent

| Example No. | Reagents | Isosorbide: base, mole ratio | React Time hrs. | Temp. °C. | DMI % Total Yield GLC est. | Isolated Yields |
|---|---|---|---|---|---|---|
| 12 | 2 mole isosorbide + 4.5 mole NaOH + 250 ml DMSO + 25 ml H₂O | 1:2.25 | 6.0 | 81 | 95% | 243 g DMI (72%) |
| 13 | 0.68 mole isosorbide + 2.5 mole NaOH + 200 ml toluene + 25 ml DMSO | 1:3.7 | 8.0 | 80 | 60% | |
| 14 | 2 mole isosorbide + 5 mole NaOH + 150 ml DMSO | 1:2.5 | 5.0 | 84 | 98% | 273,5 g (78.5%) |
| 15 | 2 mole isosorbide + 5 mole NaOH + 150 ml DMSO[1] | 1:2.5 | 4.0 | 84 | 98% | 305 g (87.5%) |
| 16 | 2 mole isosorbide + 5 mole NaOH + 100 ml DMSO | 1:2.5 | 5.25 | 86 | 90% | 261.5 g (75%) |
| 17 | 2 mole isosorbide + 5 mole NaOH + 50 ml DMSO | 1:2.5 | 7.5 | 86 | 90% | 243.1 g |
| 18 | 2 mole isosorbide + 50 ml DMSO + 5.25 mole NaOH | 1:2.63 | 5.0 | 86 | 90% | 254. g (73%) |

[1] worked up by extraction with ethylacetate.

TABLE 3
DMI from Soribtol in One Pot

| Example No. | Reagents | Isosorbide: base, mole ratio | React Time hrs. | Temp. °C. | Isolated Yields |
|---|---|---|---|---|---|
| 19 | 2 mole soribtol + 5.6 g H₂SO₄ + 600 ml toluene + 6.5 mole NaOH + 19.2 g TBABr | 1:3.25 | 7.5 | 85 | 144.4 g (41%) |
| 20 | 2 mole sorbitol + 5.8 g H₂SO₄ + 600 ml toluene + 6 mole NaOH + 200 ml DMSO | 1:3.0 | 7.0 | 86 | 185.5 g (53%) |
| 21 | 2 mole sorbitol + 4.0 g H₂SO₄ + 600 ml toluene (removed) + 7 mole NaOH + 200 ml DMSO | 1:3.5 | 6.5 | 85 | 199 g (57%) |

What is claimed is:

1. An improved high yield process for the polyalkylation of hexitols and inner ether derivatives thereof to form polyalkyl ether derivatives of said hexitols which comprises the steps of:
   (a) forming an aqueous solution of hexitol or hexitol inner ether dispersed in an organic solvent selected from the group consisting of dimethyl sulfoxide, dimethyl acetamide, dimethyl formamide, toluene, xylene, bis(2-methoxyethyl)ether, and ethyleneglycoldiethyl ether to form an aqueous dispersion,
   (b) forming a monoalkali metal alkoxide of said hexitol or hexitol inner ether by the addition of sodium or potassium alkali to said dispersion,
   (c) forming a monoalkyl ether and the halide salt of sodium or potassium from said monoalkali metal alkoxide by the addition of an alkyl monohalide having 1-4 carbon atoms to said dispersion,
   (d) continuing the alkylation of said formed monoalkyl ether by the addition to said dispersion of substantially stoichiometric amounts of said alkyl monohalide and substantially stoichiometric amounts of said alkali such that no more than a monoalkali metal alkoxide derivative is present in said dispersion until a completely polyalkylated hexitol or hexitol inner ether is produced, and
   (e) separating said produced polyalkylated hexitol or hexitol inner ether from said aqueous dispersion.

2. A process of claim 1 wherein steps (a) through (d) are carried out at a temperature of 60°-120° C.

3. A process of claim 1 wherein said process steps (a) through (d) are carried out at 80°-90° C.

4. A process of claim 1 wherein said hexitol and inner ethers thereof are selected from sorbitol, mannitol, sorbitan, mannitan, isosorbide and isomannide.

5. A process of claim 1 wherein said inner ether is isosorbide, said alkyl halide is methyl chloride and said organic solvent is selected from dimethyl sulfoxide, toluene and mixtures thereof.

6. A process of claim 1 wherein the solvent in step (a) is dimethyl sulfoxide and step (e) is carried out by solvent extraction using a nonpolar aromatic solvent to remove the completely alkylated product from the dimethyl sulfoxide-water-chloride salt residue.

7. A process of claim 6 wherein said aromatic solvent is toluene.

8. A process of claim 1 wherein said process steps (a)-(d) is carried out with aromatic hydrocarbon solvent and a phase transfer catalyst.

9. A process of claim 8 wherein said phase transfer catalyst is selected from the group consisting of tetrabutyl ammonium bromide, and tetrabutyl ammonium sulfate.

* * * * *